United States Patent
Beymer

(10) Patent No.: US 7,556,377 B2
(45) Date of Patent: Jul. 7, 2009

(54) SYSTEM AND METHOD OF DETECTING EYE FIXATIONS USING ADAPTIVE THRESHOLDS

(75) Inventor: David James Beymer, San Jose, CA (US)

(73) Assignee: International Business Machines Corporation, Armonk, NY (US)

(*) Notice: Subject to any disclaimer, the term of this patent is extended or adjusted under 35 U.S.C. 154(b) by 96 days.

(21) Appl. No.: 11/864,384

(22) Filed: Sep. 28, 2007

(65) Prior Publication Data
US 2009/0086165 A1    Apr. 2, 2009

(51) Int. Cl.
*A61B 3/14* (2006.01)
*A61B 3/10* (2006.01)

(52) U.S. Cl. .................. 351/210; 351/205

(58) Field of Classification Search ........... 351/205, 351/209–210, 221, 246
See application file for complete search history.

(56) References Cited

U.S. PATENT DOCUMENTS

| | | | |
|---|---|---|---|
| 4,755,045 A * | 7/1988 | Borah et al. ............... 351/210 |
| 5,726,916 A | 3/1998 | Smyth | |
| 6,090,051 A | 7/2000 | Marshall | |
| 6,102,870 A | 8/2000 | Edwards | |
| 6,120,461 A | 9/2000 | Smyth | |
| 2005/0073136 A1 * | 4/2005 | Larsson et al. ............... 280/735 |

OTHER PUBLICATIONS

Salvucci, D. D. and Goldberg, J. H. 2000. Identifying fixations and saccades in eye-tracking protocols. In Proceedings of the 2000 Symposium on Eye Tracking Research & Applications (Palm Beach Gardens, Florida, United States, Nov. 6-8, 2000). ETRA '00. ACM Press, New York, NY, 71-78.

* cited by examiner

*Primary Examiner*—Scott J Sugarman
*Assistant Examiner*—Dawayne A Pinkney
(74) *Attorney, Agent, or Firm*—Shimokaji & Associates, P.C.

(57) ABSTRACT

A system and method of adaptively establishing fixation thresholds for eye-gaze tracking data and identifying fixations within the eye-gaze tracking data are disclosed. Eye-gaze tracking data is collected. A saccade estimate may be calculated using a percentile statistic of the changes in eye-gaze position. Fixations may be determined by comparing the saccade estimates with the changes in eye-gaze positions over time windows.

17 Claims, 7 Drawing Sheets

SYSTEM AND METHOD OF DETECTING EYE FIXATIONS USING ADAPTIVE THRESHOLDS

BACKGROUND OF THE INVENTION

The present invention relates generally to eye gaze tracking system and, more particularly, to eye gaze tracking including adaptive fixation estimation.

In eye gaze tracking, a camera placed near a visual display records graphical data including the position of the user's pupils and the locations of reflected glints from infrared LEDs. By processing the graphical data and calibrating the position of the pupil and glints with the visual display, a streaming estimate of the spot on the display viewed by the user may be generated and recorded as a stream of gaze points (x, y, t).

Gaze tracking provides actual and potentially real-time knowledge of a viewer's attention including places on the screen that draw attention first, the length of time the user spends looking at any given place, and the sequence of places receiving attention. For some applications, gaze tracking can produce results that seem akin to mind reading by accessing a user's unconscious processes. The technology has found use in a wide variety of applications. For example, a gaze tracking stream in real time has been used to augment a graphical user interface. Objects represented on a computer screen may be selected or even accessed simply by looking at object. A prototype human-computer dialog system uses eye gaze tracking to provide visual context to the user's speech. For example, a virtual tourist application may use gaze tracking to provide the antecedent when a user makes an otherwise vague statement like "I would like to stay in this hotel." In an eye gaze analytics application, eye gaze tracking can be recorded while subjects are navigating the web or testing a novel interface. Analysis of the recorded gaze tracking data may provide otherwise inaccessible feedback for web or interface design.

A typical eye gaze tracking system may consist of hardware including a visual display, camera and processor with image processing software to estimate and record the points of focus of a user's gaze. Higher level applications may be implemented to use or interpret gaze.

When a stream of eye gaze tracking data is analyzed, the first step is typically the identification of groups of data points that together represent eye fixations. Fixations are defined as a brief period of time (e.g., ¼ sec) where the point of focus of the eye is relatively stationary. A fixation represents a span of time where the user's attention is fixated on a discrete portion of the visual stimulus. When the fixation comes to an end, the eyes execute a sudden motion called a saccade, moving the user's attention to another fixation point where the user examines another discrete portion of the stimulus.

Fixation is a natural part of our vision. The physiology of the human eye dictates the specifics of these fixations as much as our conscious attempts at attention. As such, fixations are best defined by observation and can only be weakly controlled by engineering and design. After fixations are determined and detected, they can be used for higher level applications, such as telling when the user is gazing at a particular button or reading across a line of text. Good performance at the application level depends critically on good fixation detection.

Fixation detection depends on defining thresholds to select the gaze points representing a fixation within a compact spatial-temporal region. For example, in dispersion-based fixation detection, a fixation may be defined as a set of consecutive gaze points that span a time interval longer than some minimum threshold (e.g., 100 milliseconds) and have a spatial deviation that is less than a selected spatial threshold.

Complicating the detection of eye fixations is the continual presence of small eye motions called microsaccades as well as system noise. Microsaccades represent small deviations in the point of focus around an otherwise specific gaze location. The specific implementations of eye-gaze tracking systems also introduce some level of noise into the data, as the motion of the eyes, video acquisition, and the calibration limits make precise gaze tracking impossible. Additive random noise is especially amplified in remote eye trackers where the camera is placed near the monitor and thus usually a few feet from the user. These factors may vary between system implementations, users and the content being viewed, making it difficult to select a universally applicable set of spatial thresholds.

Current fixation detection methods may use fixed thresholds that may be manually set by an eye tracking operator or analyst. For example, using a dispersion threshold of ½ to 1 degree of visual angle of the user's eye has been recommended. Known commercial systems recommend a threshold of 50 pixels if the user is looking at pictures, 20 pixels if the user is reading, and 30 pixels for "mixed" content. Using fixed thresholds limits the generality of fixation detection and requires manual fine tuning. Thresholds that are too small may result in missed fixations, while thresholds that are too large may result in over-grouping fixations, which erroneously combines consecutive fixations together. Fixed thresholds may prevent implementation of a universal "plug and play" eye gaze tracker system, requiring a skilled operator to appropriately adjust fixation thresholds.

Gaze tracking data may be processed using a Gaussian filter, smoothing the data from the x and y channels. Noise reduction tends to smear fixations together, potentially blurring the boundary between fixations and saccades. The transitions from fixation to saccade may contain high frequency information that may be lost by this type of filtering process.

What is needed, therefore, is a gaze tracking system that can determine fixations in the gaze tracking data without assigning fixed thresholds.

SUMMARY OF THE INVENTION

In one embodiment of the present invention, an adaptive eye-tracking system comprises a visual display having display points represented by display point coordinates and display data including display point coordinates. A camera records video data of the user's eye, including time stamps. A processor analyzes the eye video to estimate gaze, associating the eye gaze positions with display point coordinates, calculating a gaze noise value using the eye gaze positions, calculating a saccade estimate using the gaze noise value and determining display point coordinates representing fixations using the saccade estimate and the associated eye gaze positions.

In another embodiment of the present invention, an adaptive eye-tracking method comprises recording eye-gaze positions, calculating a saccade estimate using the recorded eye-gaze positions and determining eye-gaze fixations using the recorded eye-gaze positions and the saccade estimate.

In another embodiment of the present invention, a computer program product, for use with an eye-gaze tracking system, comprises a computer useable medium including a computer readable program, wherein the computer readable program when executed on a computer causes the computer to generate eye-gaze tracking data, the eye-gaze tracking data including data points defined by a first coordinate value, a second coordinate value and a time-stamp value. A first coordinate percentile statistic is calculated from the first coordinate values of the data points. A first coordinate saccade estimate is calculated from the first coordinate percentile statistic. A second coordinate percentile statistic is calculated from the second coordinate values of the data points. A second coordinate saccade estimate is calculated from the second coordinate percentile statistic. The presence of a fixation in a series of data points having sequential time-stamp values is determined by comparing the dispersion in first coordinate values with the first coordinate saccade estimate and comparing the dispersion in second coordinate values with the second coordinate saccade estimate. The first coordinate values, second coordinate values, and beginning and ending time-stamp values of the fixation are indicated.

These and other features, aspects, and advantages of the present invention will become better understood with reference to the following drawings, description, and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention comprises an eye-gaze tracking system that determines fixation thresholds using collected eye-tracking data. An adaptive system for determining eye-gaze fixations is disclosed. Eye-gaze position data may be analyzed by calculating saccade estimates for each point. The changes in eye-gaze position may be compared to the saccade estimate for the point. Where the eye-gaze position changes are less than the saccade estimate and persist for a determined period of time, a fixation may be noted. The saccade estimates may be calculated for both the horizontal and vertical directions. An eye-tracking system including adaptive fixation threshold determination can be used in design applications to provide feedback from the user, particularly where the content of the designs are varied.

Prior art eye-gaze tracking systems typically use fixed or manually changed fixation thresholds. In contrast, an eye-gaze tracking system with adaptive threshold determination, as with embodiments of the present invention, allows the gaze-tracking system to establish appropriate fixation thresholds without the use of fixed or manually changed fixation thresholds.

Figure 1:
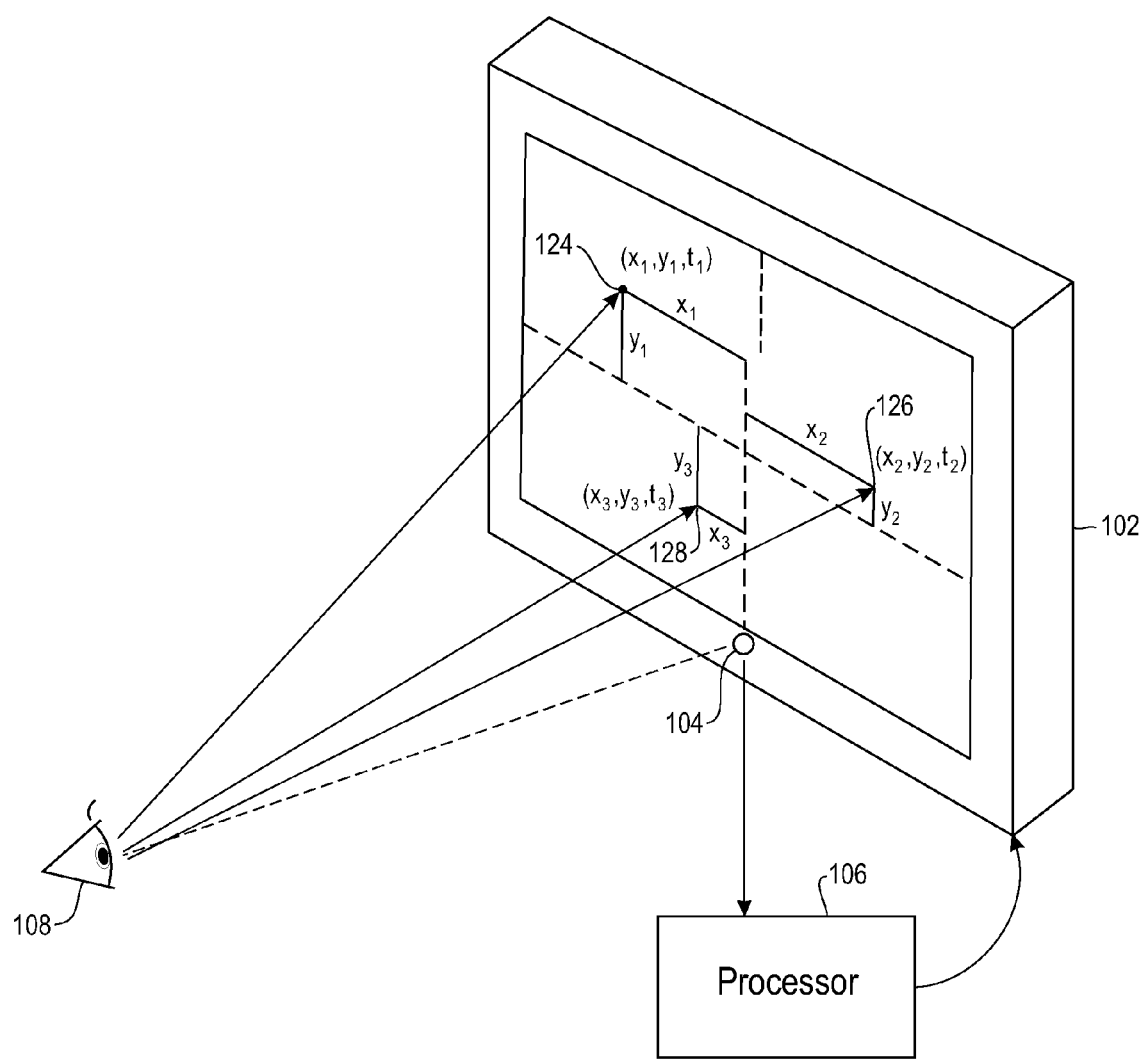
FIG. 1 is system architecture diagram illustrating a system for eye-gaze tracking in accordance with an embodiment of the invention.

With reference to FIG. 1, an eye gaze tracking system 100 is shown. A display 102 such as a cathode ray tube, LCD display or any suitable display unit, may be positioned near a camera device 104 so that the view of the camera 104 may be fixed relative to the display 102. In accordance with an embodiment of the invention, the camera 104 may be integrated into the frame of the display 102. Alternatively, the camera 104 may be affixed to the exterior of the display 102 at the top, bottom or either side of the display. Some systems allow for camera motion to keep the user's head within the camera field of view. In these systems, camera motion is modeled and calibrated with regards to the display.

Within the field of view of the camera 104, an observer's eye 108 views content such as text, graphical images, video or any other suitable visual data on the display 102. A processor 106 provides the data positioned on the screen of the display 102, preferably tracking the position of the displayed data on the display 102 in time. The processor 106 receives data from the camera 104. The data received from the camera 104 may be processed by the processor 106 to determine motion of the eye 108, particularly movement of the pupil of the eye 108 tracking visual data in time. For example, when the observer focuses attention on a first image 124 at time t1, the camera 104 and processor 106 record the position of the eye 108.

Calibration of the system allows the processor 106 to associate the position of the eye 108 at time t1 with the screen location x1, y1 and records the data point (x1, y1, t1) to indicate the spot 124 on the display 102 viewed by the observer at time t1. In accordance with an embodiment, horizontal and vertical coordinates may be designated by an x value and a y value, respectively. When the observer shifts their attention to a second spot 126, the camera 104 and processor 106 record the new position of the pupil of the eye 108 at time t2.

The processor 106 associates the position indicated by the camera 104 with the spot 126 at coordinates x2, y2 and records the data point (x2, y2, t2). When the observer shifts attention to a third spot 128, the processor records data point (x3, y3, t3). For clarity, the sequence of data points (x1, y1, t1), (x2, y2, t2) and (x3, y3, t3) represent large jumps over display 102.

In practice, the time increments implemented are on the order of tenths of a second and the typical distance between the points viewed on the display are on the order of millimeters. The data points may be recorded by the processor for later analysis or may be analyzed in real-time, depending on the particular purpose of the eye gaze detection.

Figure 2:
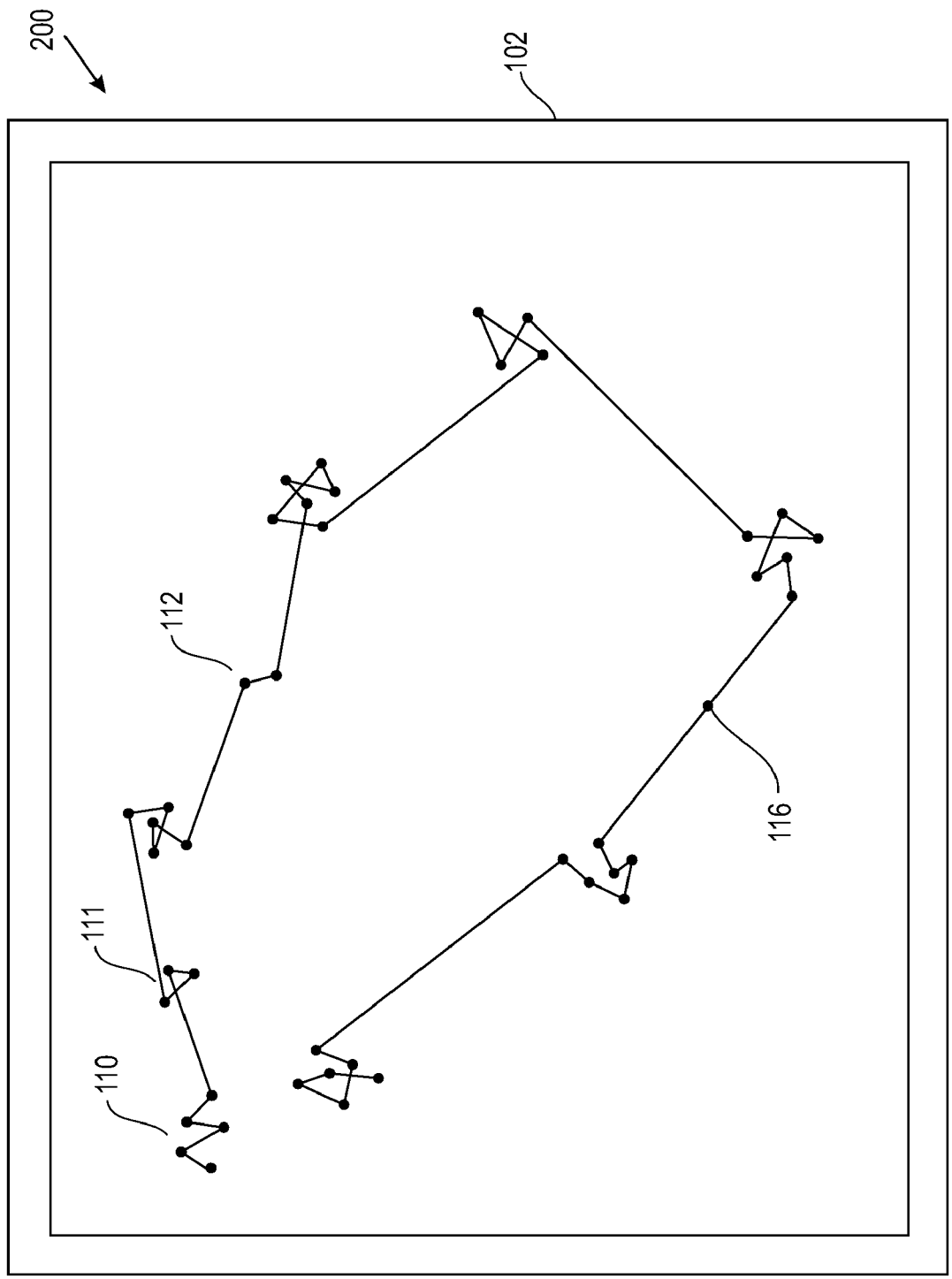
FIG. 2 is a map overlay of exemplary eye-gaze position points on a display in accordance with an embodiment of the invention

With reference to FIG. 2, a display 102 with an overlay indicating discrete eye gaze map 200 is shown. The map 200 represents a visual display field such as a computer monitor, screen or any other suitable space where visual data could be shown. The visual data being viewed is not represented for clarity. The map 200 consists of a sequence of data points plotted over the display field, where each data point indicates a spot on the display 102 where the gaze is directed at a given moment in time. A group of data points that are sequential in time and in a limited area on the screen define a fixation of the gaze, such as the fixation around an area 110. Because the human eye is always in motion, the actual gaze moves slightly around the area 110. This relatively small motion within a fixation is called microsaccades by psychologists and typically modeled as noise by engineers.

After viewing the first area 110 for a short time, the gaze moves to view a second spot 111. The larger motion, ending one fixation and beginning another fixation, is called a saccade. For the purpose of explanation, a fixation may be indicated on this map by three or more data points occurring within a small area. Although the gaze stops briefly around a third area 112, the pause is here defined as too brief to indicate gaze fixation. Data may be recorded in the process of a saccade, for example as the gaze moves through data point 116. The spatial variance and duration of the gaze defining fixations and saccades are different for varieties of visual data types, individuals and purposes. For example, the gaze fixation of a proofreader working on a text may be orders of magnitude different than the gaze fixation of a jet pilot in flight.

Figure 3:
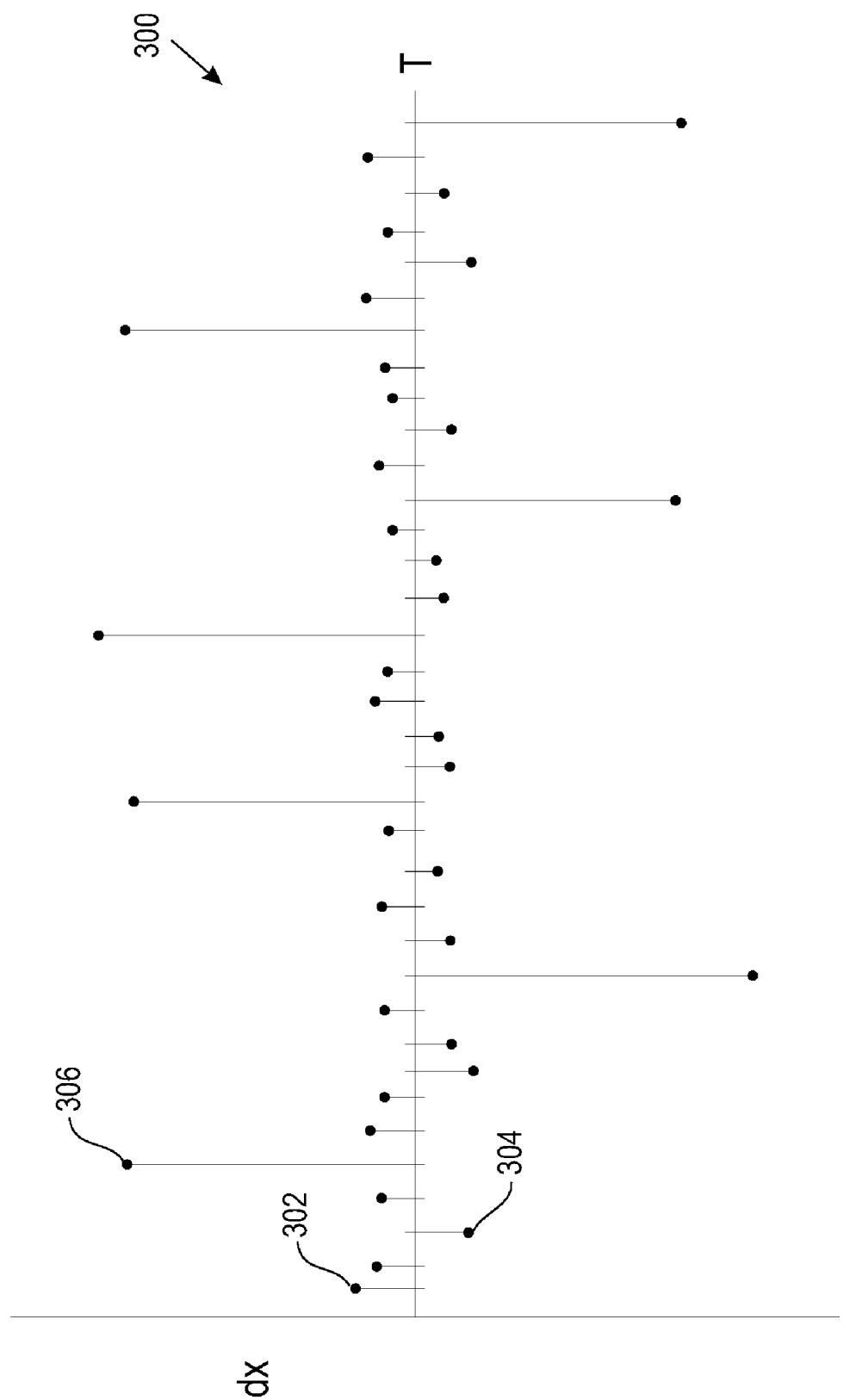
FIG. 3 is a plot of exemplary changes in eye-gaze position in accordance with an embodiment of the invention.

With reference to FIG. 3, a plot 300 representative of exemplary changes in gaze along the horizontal axis of the display 102 is shown. As the gaze moves from one spot on the display 102 to a next spot, right of the previous spot, the value of the change in x may be positive. A move to the left may be indicated by a negative value. For example, data point 302 indicates a relatively small motion of the gaze to the right of a starting point.

After a second move to the right by the gaze, the plot 300 indicates a relatively small move of the gaze to a point left 304 of the previous gaze. The gaze lingers for another time increment, moving slightly to the right. This set of small changes may indicate a fixation. When the gaze jumps a relatively larger distance to the right indicated by data point 306, a saccade may be indicated. Data may be collected over a time interval T including several fixations and saccades.

Figure 4:
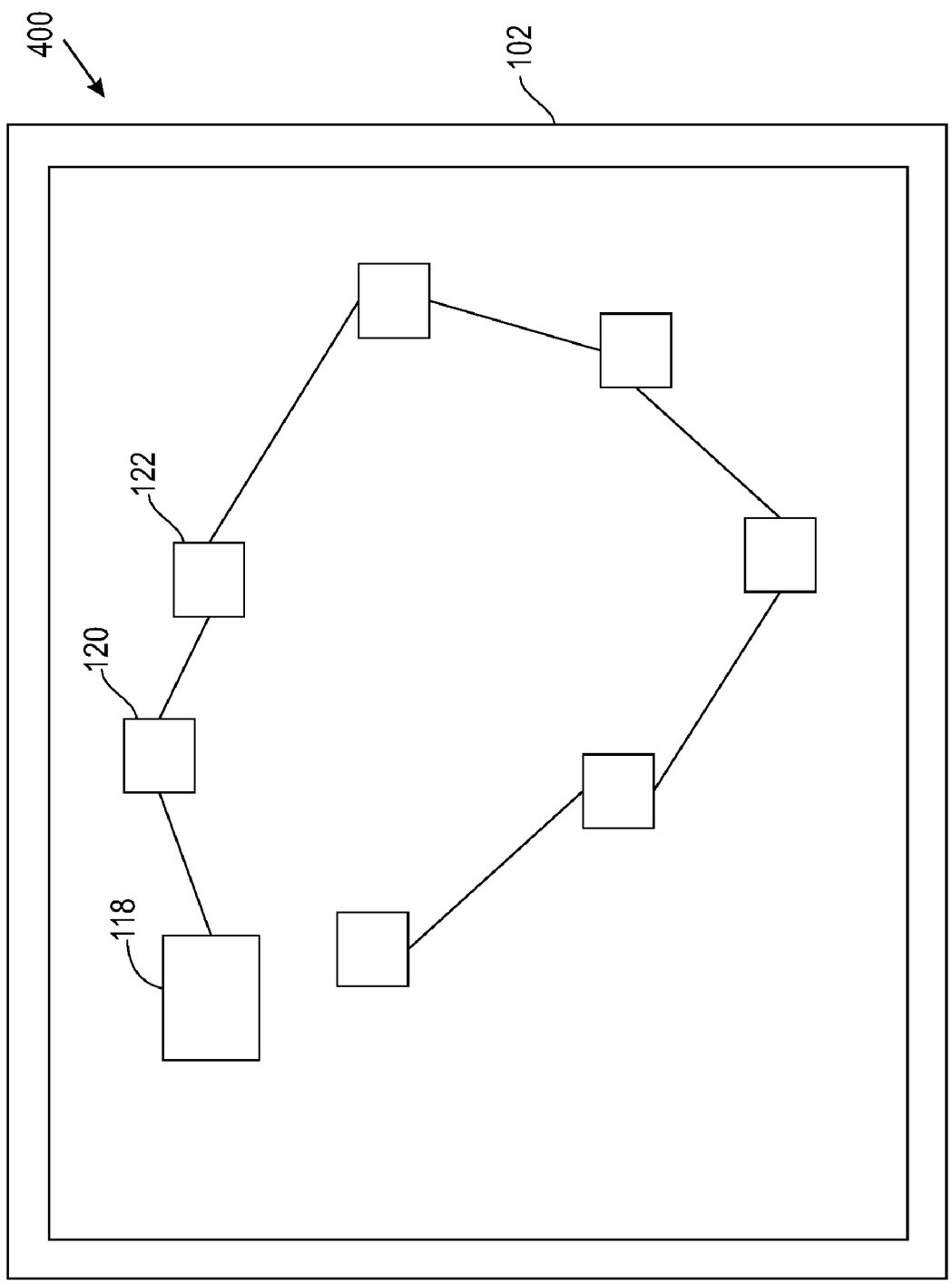
FIG. 4 is a map overlay of exemplary eye-gaze fixations on a display in accordance with an embodiment of the invention.

With reference to FIG. 4, a display 102 with an overlay map 400 of gaze fixations and saccades is shown. When data points collected during a sequence of time represent a gaze within a box 118, where the dimensions of the box 118 are indicated by analysis of the data, a fixation may be registered by the processor 106. The gaze moves into a second box 120 for a second fixation and then to a third box 122 for a third fixation. In the prior art, the dimensions of these boxes may be fixed or user-adjustable. Because the actual dimensions of a user's individual fixations may vary with the user, the visual data and the user's task, non-adaptive fixation definitions may over-generalize the space of a fixation so that only very large saccades indicate changes of fixation. Conversely, defining the fixation with overly small dimensions may over-specify the fixations, so that very few of the actual fixations are noted.

Figure 5:
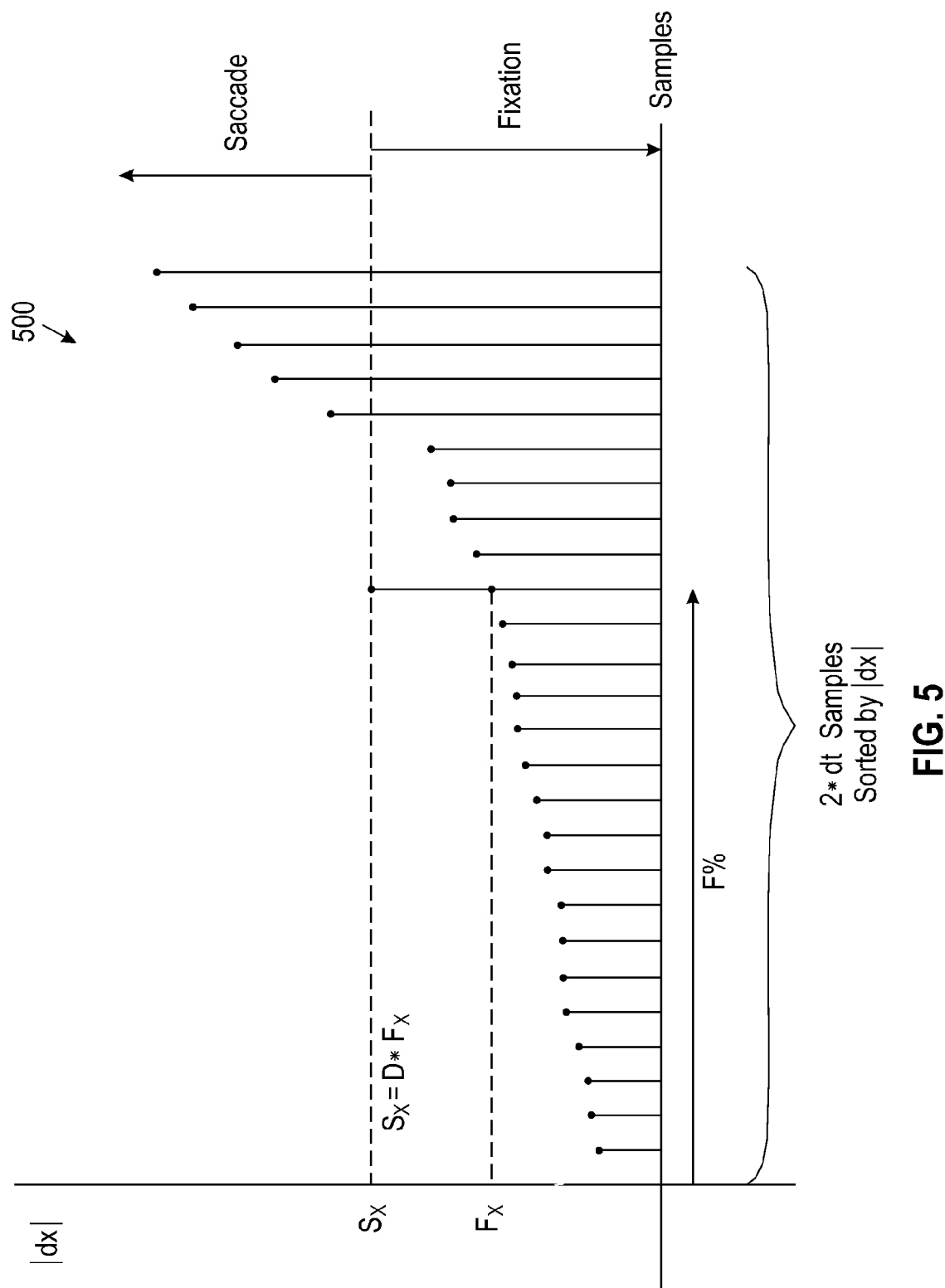
FIG. 5 is a depiction of how the percentile median statistic is used to estimate fixation detection values in accordance with the invention.

With reference to FIG. 5, a depiction 500 is shown of how percentile statistics of exemplary changes in gaze position can be used to adaptively detect fixations. Because the direction of gaze shifts are less important than the magnitude of the gaze shift, the data may be plotted using the absolute value of the change in gaze position. The absolute values of the changes in horizontal gaze position collected over a time period T and the Fth percentile statistic is computed, where F is an estimated noise fraction. FIG. 5 shows changes in gaze sorted by their absolute value only to best illustrate the median statistic computation. In best practice, efficient algorithms for finding the Fth median would be employed, avoiding more expensive sorting algorithms. In accordance with an embodiment, a noise fraction of 60% has been determined to differentiate most fixations from non-fixations. The choice of a noise fraction may depend on the system being implemented and the data being collected, as well as the preference of over-inclusion or under-inclusion when outlying data arises. The resulting value defines the gaze noise value, such that most gaze shifts smaller than the distance indicated by the gaze noise value are potentially representative of fixations. The gaze noise value may be multiplied by a dispersion factor. In accordance with an embodiment, a dispersion factor of 1.8 has been determined to differentiate a saccade from spurious changes in data values in most cases. The choice of a dispersion factor may depend on the system being implemented and the data being collected, as well as the preference between over-inclusion or under-inclusion when spurious transitions occur. The distance generated by multiplying the gaze noise value by the dispersion factor may be defined as a saccade estimate Sx. Any gaze shift change larger than the saccade estimate represents a saccade.

Figure 6:
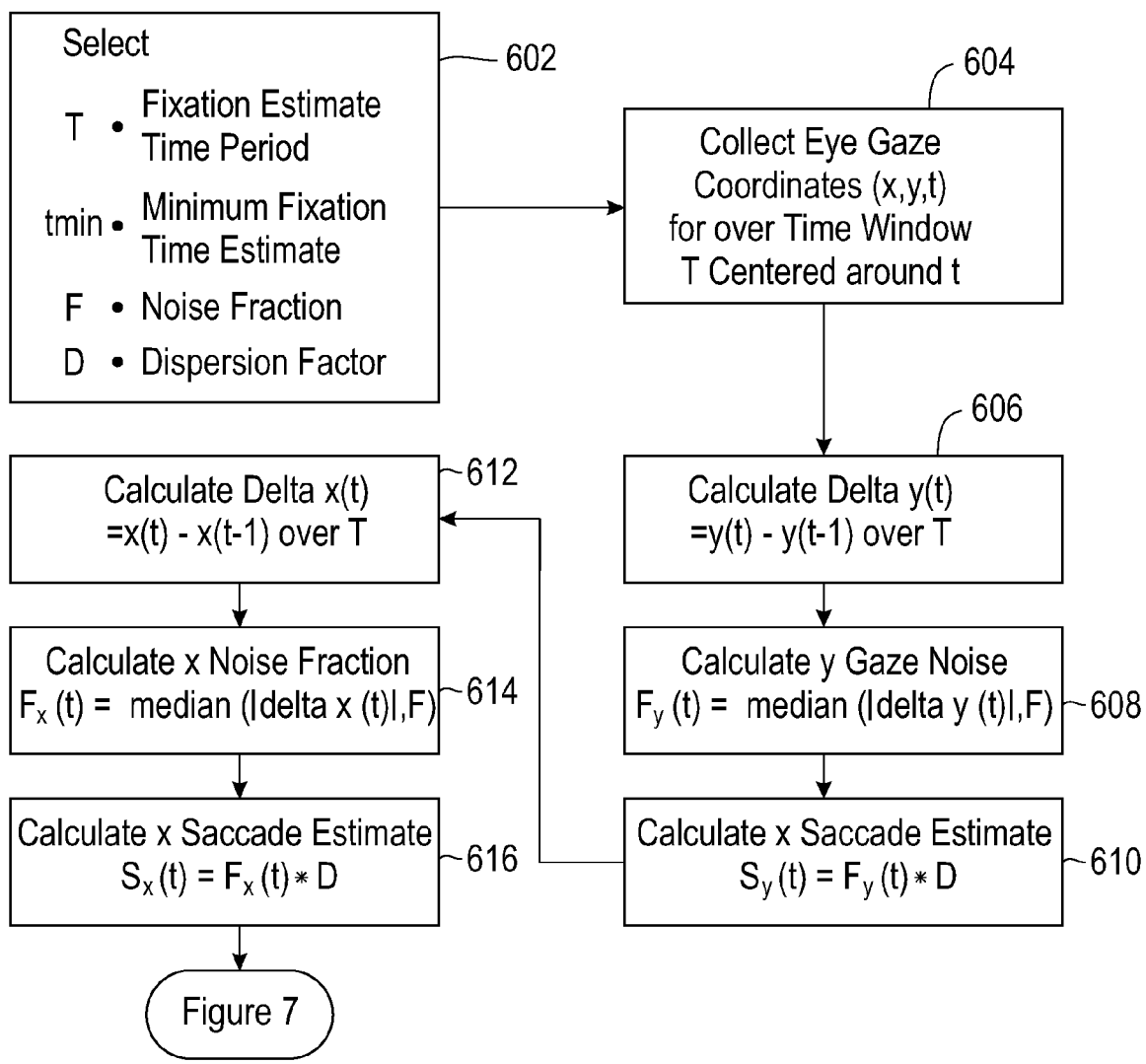
FIGS. 6 and 7 are a flowchart of a process for adaptively determining eye-gaze fixations in accordance with an embodiment of the invention.
Figure 7:
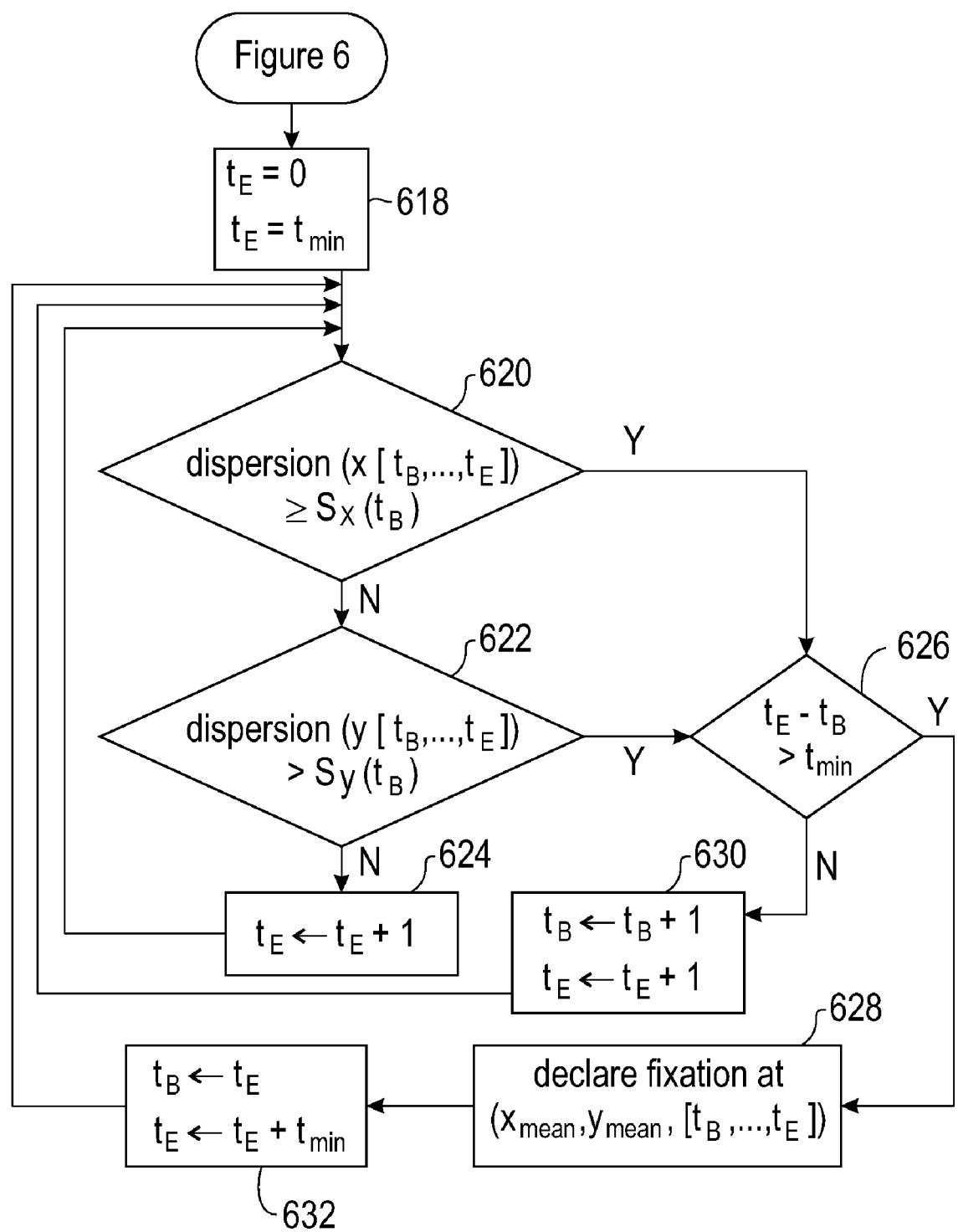

With reference to FIGS. 6 and 7, a flowchart of a process 600 to determine fixations within gaze tracking data is shown. The process begins by selection or determination of various system values at function block 602. The selected values may include the time period considered in the analysis, T, a minimum time for a fixation $t_{min}$, a noise fraction F and a dispersion factor D. The selection of the values may depend on the purpose of the eye-gaze tracking, the nature of the visual data and other considerations. Eye gaze coordinates (x, y, t) are collected at function block 604 over a time period of at least T.

Adaptive thresholds may be determined by estimating the noise levels found in both the x and y channels of the data. The estimation may be done separately for each channel since each channel often exhibits different noise characteristics. In an adaptive system, for a given a point at time t, the noise may be estimated using a local time window T representing gaze information around t. This window T may be chosen to allow the use of analytical methods from robust statistics. Data may be collected or retrieved representing the time interval [t−dt, t+dt], where 2*dt may be the size of the temporal window T. The temporal window T may be further selected to assure that, on average, a statistically adequate number of fixations are present in the time window.

Saccade estimates for x and y are then calculated from the data. Consider first the y coordinate values. The gaze measurement most indicative of the noise is the first derivative of y values, dy(t)=y(t)−y(t−1). Noisier gaze data will tend to have larger values in dy(t), since the gaze point will be jumping around. Let DY(t) be a vector aggregating all the dy(t) values in our time window [t−dt, t+dt]. Also, since we are only interested in the magnitude of noise, DY(t) will collect the absolute value of dy, |dy(t)|.

Changes in the y(t) values are calculated at function block 606, such that delta y(t) for each value of t within T is the difference between y(t) and y(t−1).

In the vector DY(t), most values will be representative of the noise. As the time window T has been selected to include multiple fixations, some dy values will represent saccades. The larger dy values will tend to represent these saccades, and the smaller values will be from the noise. This suggests using a median statistic 608 to estimate the noise Fy:

$$Fy(t) = \text{median}(DY(t), \text{noise fraction } F),$$

where "median" takes the "noise fraction" value, viewing DY(t) as a sorted list. In practice, a complete sort is unnecessary, as efficient linear-time methods exist for computing the Fth median. The noise typically represents the lower percentiles of the DY(t) distribution, and the saccades the higher percentiles. Noise will be represented by data below the "noise fraction" percentile. The y saccade estimate $S_y$ may be calculated at function block 616 by multiplying the gaze noise value $F_y$ by the dispersion factor D.

Next, the x channel is processed similarly to y in function blocks 612-616. Changes in the x(t) values are calculated at function block 612, such that delta x(t) for each value of t within T is the difference between x(t) and x(t−1). An x gaze noise value $F_x$ may be calculated at function block 614 by collecting delta x(t) for each value of t within T and computing the Fth percentile statistic. The x saccade estimate $S_x$ may be calculated at function block 616 by multiplying the gaze noise value $F_x$ by the dispersion factor D.

The process then determines which data points (x, y, t) represent fixations. Given adaptive thresholds $S_x(t)$ and $S_y(t)$, fixation detection may use a standard fixation detection algorithm such as the dispersion-based approach. To quickly summarize this process, a fixation may be declared in a time window of the gaze stream when (a) the time window may be greater than some minimum threshold (e.g., 100 milliseconds), (b) the x dispersion is $<S_x(t)$ and (c) the y dispersion is $<S_y(t)$. Dispersion is typically measured using some measure of the spread in the data, such as the standard deviation or (max-min).

Referring now to the flowchart in FIG. 7, the algorithm tests the time interval $[t_B, \ldots, t_E]$ to see if it is a fixation. The first time increment may be defined as t=0 at function block 618. Decision block 620 compares the value of dispersion of x(t) with the x saccade estimate $S_x$. If the dispersion of x(t) over the time window $[t_B, \ldots, t_E]$ is less than the x saccade estimate, the process follows the NO path, and the interval $[t_B, \ldots, t_E]$ may belong to a fixation. To continue testing this hypothesis, decision block 622 compares the dispersion of y(t) with the y saccade estimate $S_y$. If the dispersion of y(t) is less than the y saccade estimate, the process follows the NO path. While time interval $[t_B, \ldots, t_E]$ is definitely included within a fixation, the process needs to find when the fixation ends. Thus, functional block 624 increments $t_E$ and then the process tests the dispersion of the expanded time interval in 620 and 622.

If the dispersion tests in 620 or 622 show that the x or y dispersion is above the $S_x$ or $S_y$ thresholds, the process continues along the YES paths to decision block 626. Decision block 626 tests whether the time interval $t_E-t_B$ is greater than $t_{min}$. If so, the 620-622-624 loop must have detected the time interval $[t_B, \ldots, t_E-1]$ as a fixation, and the time $t_E$ is the first saccade point signaling the fixation ending point. The process follows the YES path to function block 628 and adds a new detected fixation at $(x_{mean}, y_{mean}, [t_B, \ldots, t_E-1])$, where $x_{mean}$=mean(x($t_B$), \ldots, x($t_E-1$)) and $y_{mean}$=mean(y($t_B$), \ldots, y($t_E-1$)). Function block 632 moves the time window forward to test the next $t_{min}$ time samples after the detected fixation and the process continues with the 620-622-624 loop.

Back in decision block 626, if $t_E-t_B=t_{min}$, then the process follows the NO path to function block 630. In this case, no fixation or partial fixation has been found, and the system slides its testing window $[t_B, \ldots, t_E]$ forward one unit of time to continue searching for the next fixation.

In accordance with an embodiment, the noise fraction F may be set at 60% and the dispersion factor D may be set at 1.8. Adaptive thresholds robustly detect fixations even though eye tracking noise varies considerably between individuals, and even within an individual eye tracking session.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

It should be understood, of course, that the foregoing relates to exemplary embodiments of the invention and that modifications may be made without departing from the spirit and scope of the invention as set forth in the following claims.

I claim:

1. An adaptive eye-tracking system comprising
a visual display having display points represented by display point coordinates and display data including display point coordinates;
a camera generating video data representing a user's eye viewing the visual display; and
a processor receiving said video data from said camera, estimating gaze data indicating eye-gaze positions and including time stamps, and associating said eye gaze positions with display point coordinates, calculating a gaze noise value using said eye gaze positions, calculating a saccade estimate using said gaze noise value and determining display point coordinates representing fixations using said saccade estimate and said associated eye gaze positions.

2. The adaptive eye-tracking system of claim 1, wherein said gaze noise value is calculated using changes in eye gaze positions over a period of time.

3. The adaptive eye-tracking system of claim 2, wherein said gaze noise value is calculated as a selected percentile statistic of the changes in eye gaze positions over a period of time.

4. The adaptive eye-tracking system of claim 1, wherein display point coordinates representing fixations are determined by comparing a change in eye position over a time window with the saccade estimate.

5. The adaptive eye-tracking system of claim 1, wherein said display point coordinates include horizontal and vertical coordinates.

6. The adaptive eye-tracking system of claim 5, wherein a horizontal saccade estimate is calculated and a vertical saccade estimate is calculated.

7. The adaptive eye-tracking system of claim 6 wherein display point coordinates representing fixations are determined by comparing a horizontal dispersion in eye position with a horizontal saccade estimate and by comparing a vertical dispersion in eye position with a vertical saccade estimate.

8. An adaptive eye-tracking method comprising:
recording eye-gaze positions;
calculating a saccade estimate using said recorded eye-gaze positions;
determining eye-gaze fixations using said recorded eye-gaze positions and said saccade estimate wherein said saccade estimate is calculated using a percentile statistic of the changes in eye-gaze.

9. The adaptive eye-tracking method of claim 8 where the said recorded eye-gaze positions consist of horizontal and vertical coordinates.

10. The adaptive eye-tracking method of claim 8, wherein said determining eye-gaze fixations comprises comparing the dispersion in eye-gaze positions with said saccade estimate.

11. The adaptive eye-tracking method of claim 8, wherein said saccade estimate is calculated using changes in eye-gaze positions.

12. The adaptive eye-tracking method of claim 8, further comprising associating said eye-gaze fixations with points on a display.

13. The adaptive eye-tracking method of claim 8, further comprising calibrating said eye-gaze positions such that each eye-gaze position of the recorded eye-gaze positions may be associated with a point on a display.

14. The adaptive eye-tracking process of claim 9, further comprising calculating a horizontal saccade estimate and calculating a vertical saccade estimate.

15. A computer program product for use with an eye-gaze tracking system, the computer program product comprising a computer useable medium including a computer readable program, wherein the computer readable program when executed on a computer causes the computer to:
generate eye-gaze tracking data, said eye-gaze tracking data including data points defined by a first coordinate value, a second coordinate value and a time-stamp value;
calculate a first coordinate percentile statistic from said first coordinate values of said data points;
calculate a first coordinate saccade estimate from said first coordinate percentile statistic;
calculate a second coordinate percentile statistic from said second coordinate values of said data points;
calculate a second coordinate saccade estimate from said second coordinate percentile statistic;
determine the presence of a fixation in a series of data points having sequential time-stamp values by comparing dispersion in first coordinate values with said first coordinate saccade estimate and comparing dispersion in second coordinate values with said second coordinate saccade estimate; and
indicate the first coordinate values, second coordinate values, and beginning and ending time-stamp values of said fixation.

16. The computer program product of claim 15, wherein said first coordinate value corresponds to a vertical position on a display.

17. The computer program product of claim 15, further comprising receiving eye-gaze data from a camera, wherein said eye-gaze tracking data is generated from said eye-gaze data.

* * * * *